(12) United States Patent
Matsumori

(10) Patent No.: US 6,710,046 B1
(45) Date of Patent: Mar. 23, 2004

(54) PHARMACEUTICAL COMPOSITION FOR MODULATING IMMUNITY

(75) Inventor: Akira Matsumori, Minoo (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/830,269

(22) PCT Filed: Oct. 23, 1998

(86) PCT No.: PCT/JP98/04804

§ 371 (c)(1),
(2), (4) Date: Apr. 23, 2001

(87) PCT Pub. No.: WO00/24397

PCT Pub. Date: May 4, 2000

(51) Int. Cl.[7] .................. A61K 31/50; A61K 31/501
(52) U.S. Cl. ..................... 514/252.02; 514/252.01
(58) Field of Search ....................... 514/252.02

(56) References Cited

U.S. PATENT DOCUMENTS

| | | | |
|---|---|---|---|
| 4,026,891 A | * 5/1977 | Austel et al. ............ | 260/250 |
| 4,361,563 A | 11/1982 | Austel et al. | |
| 5,286,736 A | 2/1994 | Soyka et al. | |
| 5,294,626 A | 3/1994 | Heckel et al. | |
| 5,401,738 A | * 3/1995 | Mederski et al. ........ | 514/222.5 |

FOREIGN PATENT DOCUMENTS

| | | |
|---|---|---|
| EP | 0 706 795 A2 | 4/1996 |
| EP | 0 820 990 A2 | 1/1998 |
| WO | WO 97 48697 A | 4/1996 |
| WO | WO 97 48697 | 12/1997 |

OTHER PUBLICATIONS

Akira Matsumori, Koh Ono, Yukihito Sato, Tetsuo Shioi, Yoshisuke Nose and Shigetake Sasayama—*Differential Modulation of Cytlkine Production by Drugs: Implications for Therapy in Heart Failure* J. Mol Cel Cardiol, vol. 28 pp 2491–2499 (1999); 1996 Academic Press Limited.

Matsumori et al., "Differential Modulation of Cytokine Production by Drugs: Implications for Terapy in Heart Failure", J Mol Cell Cardiol 28, 2491–2499, 1996.*

European Patent Application No. EP 0 820 992 A2, published Jan. 28, 1998, Applicant: Adir et Compagnie, in French only.

Patent Abstracts of Japan, vol. 1999, No. 09, Jul. 30 1999 & JP 11 092377 A (Nippon Boehringer Ingelheim Co Ltd), Apr. 6, 1999, Abstract (1 page).

* cited by examiner

*Primary Examiner*—Dwayne C. Jones
(74) *Attorney, Agent, or Firm*—Christie, Parker & Hale, LLP

(57) ABSTRACT

Disclosed is a pharmaceutical composition for modulating immunity, which comprises a benzimidazole, represented by the following general formula (I), a 3H tautomer, an optically active enantiomer or a pharmaceutically acceptable acid-addition salt thereof wherein, R represents an alkyl group having 1 to 5 carbon atoms, a hydroxyphenyl group or a methoxyphenyl group. This pharmaceutical composition is useful for treating cytokine-related diseases such as rheumatism, inflammation and allergy:

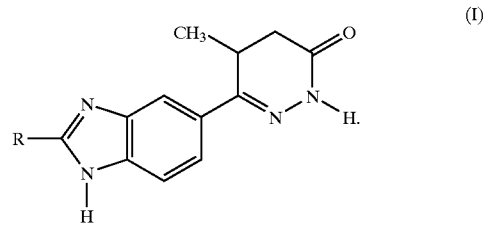

4 Claims, No Drawings

PHARMACEUTICAL COMPOSITION FOR MODULATING IMMUNITY

BACKGROUND OF THE INVENTION

The present invention relates to a pharmaceutical composition for modulating immunity, which comprises benzimidazoles, 3H tautomers, optically active enantiomers or pharmaceutically acceptable acid-addition salts thereof European Patent No. 0,008,391, discloses, in particular, 5-(5-methyl-3-oxo-4,5-dihydro-2H-6-pyridazinyl)-benzimidazole represented by the following formula I and substituted at the 2-position thereof, 3H tautomers, optically active enantiomers and pharmaceutically acceptable acid-addition salts thereof:

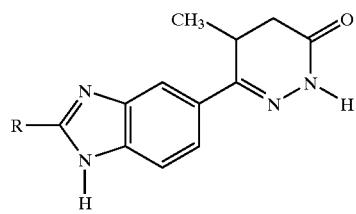

In the formula I, R represents an alkyl group having 1 to 5 carbon atoms, a hydroxyphenyl group or a methoxyphenyl group. These compounds have useful pharmaceutical characteristic properties and, in particular, show not only an anti-viral activity, an interferon-producing activity and an ulcer-inhibitory activity, but also an activity against the cardiovascular system or an activity as a cardiac, an anti-hypertensive activity and/or an anti-thrombin activity.

According to the definition, the term "activity against the cardiovascular system" means the activity, which exerts influence on the heart and blood vessels, but in this case, this activity is expressed in terms of an anti-thrombin activity and cardiac activity as well as the influence on the blood pressure, in this European Patent.

In the light of these pharmacological properties, the compounds disclosed in this European Patent, 3H tautomers, optically active enantiomers and pharmaceutically acceptable salts thereof with inorganic acids or organic acids are suitably used in the treatment of chronic heart failure or angina and/or the prophylaxis of arterial thromboembolism and arterial obstruent diseases as well as the treatment of ulcer and the extermination of viruses and viral diseases.

More specifically, these compounds have been used as therapeutic agents for treating heart failure since they have a cardiac activity and these compounds have likewise been used for treating arterial thromboembolism and arterial obstruent diseases since they have an anti-thrombin activity, in particular, an activity against platelets.

Moreover, European Patent No. 0,330,052 especially discloses a therapeutic agent containing the foregoing benzimidazole, which is represented by the general formula I and which has an anti-ischemic activity against the heart. In addition, European Patent No. 0,387,762 discloses the simultaneous use of the benzimidazole and a β-blocker, which can not only offset the muscle positive and negative inotropic effects, but also improve the heart functions under the somatically stressed conditions.

DETAILED DESCRIPTION OF THE INVENTION

It is an object of the present invention to provide a pharmaceutical composition for modulating immunity, which comprises benzimidazoles.

This and other objects of the present invention will be apparent from the following description and Examples given later.

According to the present invention, there is provided a pharmaceutical composition for modulating immunity, which comprises a benzimidazole represented by the following general formula (I), a 3H tautomer, an optically active enantiomer or a pharmaceutically acceptable acid-addition salt thereof:

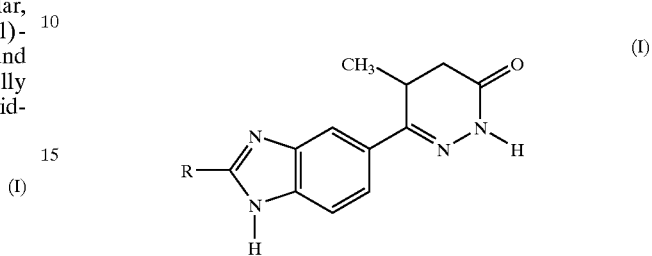

In the formula I, R represents an alkyl group having 1 to 5 carbon atoms, a hydroxyphenyl group or a methoxyphenyl group.

PREFERRED EMBODIMENTS OF THE INVENTION

Surprisingly, the benzimidazole represented by the general formula I shows an immunity-modulating effect through the reduction of a considerably high CRP value, whose normal level is not more than 0.3 mg/dl in the healthy adult (see, Robey Frank A. et al.: J. Biol. Chem. 262:7053–7057 (1987); and Kottgen Eckart et al.: J. Immunol. 149:445–453 (1992). Accordingly, it has been found that the compound is suitably used in the treatment of cytokine-related diseases such as rheumatism, inflammation, allergy, atherosclerosis, collagenous diseases, hepatitis, pancreatitis, inflammatory enteropacy, glomerulonephritis, toxic-shock syndromes, diffuse intra-intestinal coagulation syndromes, graft-versus-host diseases, tumors and immunodeficient diseases.

It has been known that pharmaceutical agents showing an effect of modulating immunity may in general be effective in the treatment of these cytokine-related diseases.

In this specification, the term "CRP" means C-reactive proteins or proteins reactive with the polysaccharides present on the bacterial cell bodies of Diplococcus pneumoniae. This is not detected in the plasma originated from normal persons and immediately appears in the blood flow when inflammation or disintegration of tissue is taken place. In a variety of infectious diseases, a large quantity of CRP appears in the blood flow within several hours after the infection and is reduced and disappears as the patients recover from the infectious diseases. Moreover, the rate of positiveness is high in case of tissue-degenerative diseases such as rheumatic fever, chronic articular rheumatism, cardiac infarction and malignant tumors. The determination of this CRP value would permit the estimation or judgment of any change in the symptoms and the degree of severity.

Preferred benzimidazoles represented by the formula I are, for instance, those represented by the formula I wherein R is a methyl group, a 2-pentyl group, a 4-methoxyphenyl group or a 4-hydroxyphenyl group and, in particular, those represented by the formula I wherein R is a 4-methoxyphenyl group or a 4-hydroxyphenyl group, in particular, a 4-methoxyphenyl group. Preferred examples thereof also include 3H tautomers, optically active enantiomers and pharmaceutically acceptable acid-addition salts thereof.

The acute toxicity of the compound represented by the general formula (I) wherein R is a 4-methoxyphenyl group or a 4-hydroxyphenyl group is known from the literatures or the like.

To achieve the desired effect of the present invention, the dose of the compound of the general formula (I) to be administered to the adult person ranges from 0.1 to 5.0 mg and preferably 1.0 to 2.5 mg when it is administered once or twice a day and, in particular, it is administered twice a day in a dose of 1.25 mg. However, the dose should be determined by the physician while taking into consideration various conditions such as the symptoms and body weights of patients to be treated, the kinds of selected compounds to be administered and the route of administration selected. Therefore, the present invention is not restricted to the foregoing specific dosage range.

To use the compounds as pharmaceutical agents, the foregoing active substance is blended with at least one member selected from the group consisting of inert conventionally used carriers and/or diluents such as corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetyl stearyl alcohol, carboxymethyl cellulose or fatty substances such as hydrogenated oil to form conventional galenical preparations such as tablets free of any coating, coated tablets, capsules, powders, suspensions, drops, ampuls, syrups or suppositories. The composition of the present invention can be administered through a variety of administration routes such as oral and per rectum routes, as well as local or parenteral routes, for instance, injection or inhalation.

The effects of these compositions are determined according to the following methods.

2-(4-Methoxyphenyl)-5-(5-methyl-3-oxo-4,5-dihydro-2H-6-pyridazinyl)-benzimidazole (hereunder referred to as imobendan was orally administered to a patient who suffered from heart failure while malignant articular rheumatism set in as a complication and the CRP value thereof was determined with the elapse of time.

The CRP value was determined by the latex agglutination assay disclosed in Senju Osamu, et al.: J. Clin. Lab. Immunol. 19:99–103(1986) according to a method identical to that disclosed in Claus David R. et al.: J. Lab. Clin. Med. 87:120–128(1976).

The CRP value of the patient prior to the administration of Pimobendan was found to be 4.7 mg/dl. When Pimobendan was administered to the patient in a dose of 1.25 mg, the CRP value thereof was reduced and therefore, the compound was administered in a dose of 1.25 mg twice a day on and after the next day (this was defined to be the day at which the administration was initiated).

The patient was subjected to the echocardiography and as a result, it was found that the heart function was improved. Thus, the administration of Pimobendan was discontinued. Thereafter, Pimobendan was again administered to the patient in a dose of 1.25 mg twice a day to confirm the effect of the drug to reduce the CRP value. As a result, it was found that the CRP value was again reduced and the inflammation due to the malignant articular rheumatism was recovered.

The following Table 1 shows a part of the CRP values determined during the foregoing test period.

TABLE 1

| Days After Initiating the Administration | CRP Value (mg/dl) |
|---|---|
| 12 | 1.7 |
| 28 | 6.1 |
| 61 | 3.0 |
| 71 | 3.3 |
| (89) | (5.0) |
| (90) | (2.7) |
| (97) | (2.4) |
| (105) | (3.6) |
| (113) | (3.2) |
| (119) | (2.9) |
| 126 | 3.0 |
| 127 | 4.3 |
| 130 | 3.8 |
| 132 | 2.1 |
| 137 | 1.3 |

Note: The numerical value given in parentheses represents the day at which any Pimobendan was not administered.

The results listed in Table 1 clearly indicate that the compound administered could appropriately reduce the CRP value to a clinically satisfactory level.

This novel finding clearly suggests that the composition of the present invention, in particular, Pimobendan is suitably used in the treatment of cytokine-related diseases.

Thus, according to the present invention, there can be provided a pharmaceutical composition showing the immunity-modulating effect through the reduction of the abnormally high CRP value.

The present invention will more specifically be described below with reference to the following Examples, but the present invention is not restricted to these specific Examples at all.

EXAMPLE 1

Preparation of Tablets Containing 0.5 mg of 2-(4-methoxyphenyl)-5-(5-methyl-3-oxo-4,5-dihydro-2H-6-pyridazinyl)-benzimidazole

| COMPOSITION | |
|---|---|
| (01) Active Component | 0.50 mg |
| (02) Lactose | 47.50 mg |
| (03) Corn Starch | 70.00 mg |
| (04) polyvinyl Pyrrolidone | 8.00 mg |
| (05) Aerosil | 3.00 mg |
| (06) Magnesium Stearate | 1.00 mg |
| Total | 130.00 mg |

Preparation: The foregoing substances (01) to (03) were mixed together, followed by converting the resulting mixture, together with an ethanol solution of the substance (04), into particles, drying and classification of the resulting particles, mixing the particles with the components (05) and (06) and compression of the resulting mixture into tablets.

EXAMPLE 2

Preparation of Tablets Containing 1.25 mg of 2-(4-methoxyphenyl)-5-(5-methyl-3-oxo-4,5-dihydro-2H-6-pyridazinyl)-benzimidazole

| COMPOSITION | |
|---|---|
| (01) Active Component | 1.25 mg |
| (02) Lactose | 66.75 mg |
| (03) Corn Starch | 70.00 mg |
| (04) polyvinyl Pyrrolidone | 8.00 mg |
| (05) Aerosil | 3.00 mg |
| (06) Magnesium Stearate | 1.00 mg |
| Total | 150.00 mg |

Preparation: The foregoing substances (01) to (03) were mixed together, followed by converting the resulting mixture, together with an ethanol solution of the substance (04), into particles, drying and classification of the resulting particles, mixing the particles with the components (05) and (06) and compression of the resulting mixture into tablets.

EXAMPLE 3

Preparation of Capsules Containing 2.00 mg of 2-(4-methoxyphenyl)-5-(5-methyl-3-oxo-4,5-dihydro-2H-6-pyridazinyl)-benzimidazole

| COMPOSITION | |
|---|---|
| (01) Active Substance | 2.00 mg |
| (02) Lactose | 95.00 mg |
| (03) Corn Starch | 40.00 mg |
| (04) Aerosil | 2.00 mg |
| (05) Magnesium Stearate | 1.00 mg |
| Total | 140.00 mg |

Preparation: The foregoing substances (01) to (05) were mixed together and then the resulting mixture was filled in Size 4 capsules.

EXAMPLE 4

Preparation of Tablets Containing 2.50 mg of 2-(4-methoxyphenyl)-5-(5-methyl-3-oxo-4,5-dihydro-2H-6-pyridazinyl)-benzimidazole

| COMPOSITION | |
|---|---|
| (01) Active Component | 2.50 mg |
| (02) Lactose | 59.50 mg |
| (03) Corn Starch | 50.00 mg |
| (04) Polyvinyl Pyrrolidone | 5.00 mg |
| (05) Aerosil | 2.00 mg |
| (06) Magnesium Stearate | 1.00 mg |
| Total | 120.00 mg |

Preparation: The foregoing substances (01) to (03) were mixed together, followed by converting the resulting mixture, together with an ethanol solution of the substance (04), into particles, drying and classification of the resulting particles, mixing the particles with the components (05) and (06) and compression of the resulting mixture into tablets each having a diameter of 7 mm.

EXAMPLE 5

Preparation of Coated Tablets, with Notches for Cutting into Small Pieces, Containing 1.00 mg of 2-(4-methoxyphenyl)-5-(5-methyl-3-oxo-4,5-dihydro-2H-6-pyridazinyl)-benzimidazole

| COMPOSITION | |
|---|---|
| (01) Active Component | 1.00 mg |
| (02) Lactose | 61.00 mg |
| (03) Corn Starch | 50.00 mg |
| (04) Polyvinyl Pyrrolidone | 5.00 mg |
| (05) Aerosil | 2.00 mg |
| (06) Magnesium Stearate | 1.00 mg |
| Total | 120.00 mg |

Preparation: The foregoing substances (01) to (03) were mixed together, followed by converting the resulting mixture, together with an ethanol solution of the substance (04), into particles, drying and classification of the resulting particles, mixing the particles with the components (05) and (06) and compression of the resulting mixture into cores for coated tablets each having a diameter of 7 mm. Then the resulting cores were coated with a coating agent according to the conventional method.

What is claimed is:

1. A method of treatment of rheumatism, hepatitis or pancreatitis comprising the step of administering, to a patient, a benzimidazole represented by the following general formula (I), a 3H tautomer, an optically active enantiomer or a pharmaceutically acceptable acid-addition salt thereof:

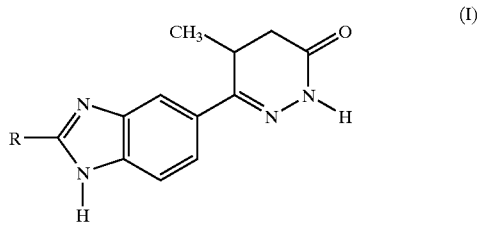

wherein, R represents an alkyl group having 1 to 5 carbon atoms, a hydroxyphenyl group or a methoxyphenyl group.

2. The method of claim 1 wherein the substituent R in the formula (I) represents a 4-methyl, 2-pentyl, 4-methoxyphenyl or 4-hydroxyphenyl group.

3. The method of claim 1 wherein the substituent R in the formula (I) represents a 4-methoxyphenyl or 4-hydroxyphenyl group.

4. The method of claim 1 wherein the substituent R in the formula (I) represents a 4-methoxyphenyl group.

* * * * *

UNITED STATES PATENT AND TRADEMARK OFFICE
CERTIFICATE OF CORRECTION

PATENT NO.      : 6,710,046 B1
DATED           : March 23, 2004
INVENTOR(S)     : Matsumori It is certified that error appears in the above-identified patent and that said Letters Patent is hereby corrected as shown below:

Title page,
Item [56], References Cited, FOREIGN PATENT DOCUMENTS,
delete "WO     WO 97 48697 A          4/1996".
OTHER PUBLICATIONS, delete "Akira Matsumori, Koh Ono, Yukihito Sato, Tetsuo Shioi, Yoshisuke Nose and Shigetake Sasayama - Differential Modulation of Cytlkine Production by Drugs: Implications for Therapy in Heart Failure J Mol Cel Cardiol, vol. 28 pp 2491-2499 (1999); 1996 Academic Press Limited.";
"Matsumori et al." reference, delete "Terapy" insert -- Therapy --.

Column 6,
Line 56, delete "4-methyl", insert -- methyl --.

Signed and Sealed this

Eighth Day of November, 2005

JON W. DUDAS
*Director of the United States Patent and Trademark Office*